United States Patent [19]

Tsubouchi et al.

[11] Patent Number: 4,521,324

[45] Date of Patent: Jun. 4, 1985

[54] FLUID FOR TRACTION DRIVE

[75] Inventors: Toshiyuki Tsubouchi, Sodegaura; Hitoshi Hata, Ichihara, both of Japan

[73] Assignee: Idemitsu Kosan Company Limited, Tokyo, Japan

[21] Appl. No.: 539,980

[22] Filed: Oct. 7, 1983

[30] Foreign Application Priority Data

Oct. 14, 1982 [JP] Japan ................................ 57-179078

[51] Int. Cl.³ ........................ C10M 1/02; C07C 13/605
[52] U.S. Cl. ........................................... 252/73; 252/9;
252/52 R; 208/14; 585/21; 585/22; 585/23;
585/26; 585/27; 585/360; 74/200
[58] Field of Search ........................... 252/9, 52 R, 73;
208/14; 585/21, 22, 23, 26, 27, 360; 74/200

[56] References Cited

U.S. PATENT DOCUMENTS 3,336,407 8/1967 Bushick ................................... 585/27
3,411,369 11/1968 Hammann et al. .................. 252/52 R

*Primary Examiner*—Paul Lieberman
*Assistant Examiner*—Robert A. Wax
*Attorney, Agent, or Firm*—Walter H. Schneider

[57] ABSTRACT

A fluid for traction drive is described, containing a liquid material as a base stock wherein the liquid material is prepared by bringing naphthalene or tetralin into contact with a Friedel-Crafts catalyst and then hydrogenating the resulting compounds. This traction drive fluid exhibits a superior traction coefficient from low temperature to elevated temperature and further has a low viscosity. Thus the fluid contributes to the production of small-sized drive mechanisms and can be widely used in various machines.

10 Claims, 1 Drawing Figure

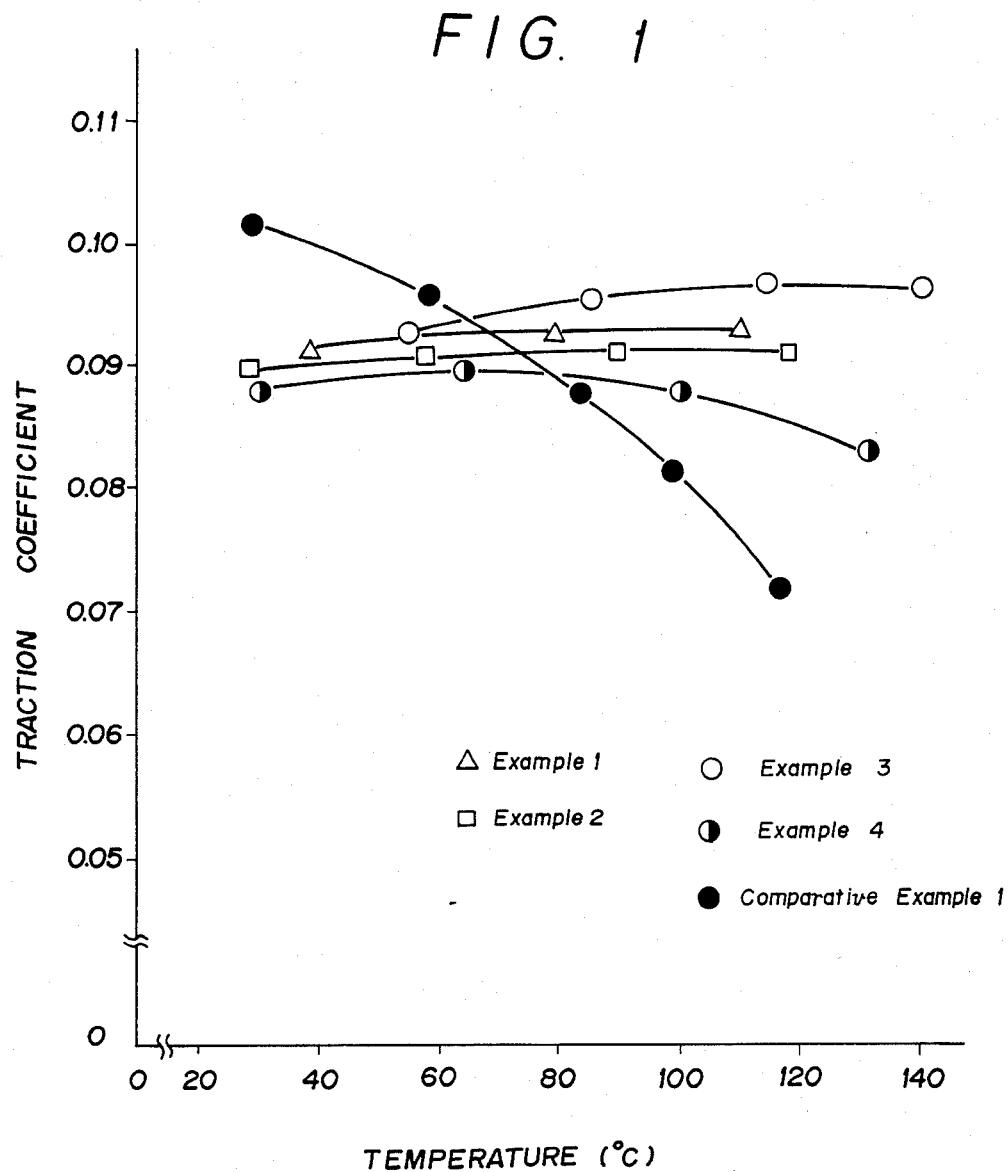

FLUID FOR TRACTION DRIVE

FIELD OF THE INVENTION

The present invention relates to a fluid for traction drive, a fluid for use in the traction drive mechanism, and more particularly, to a traction drive fluid having a low viscosity and a reduced temperature dependence of traction coefficient.

BACKGROUND OF THE INVENTION

In general, the traction drive mechanism is preferably of as small a size as possible from a viewpoint of energy-saving. Furthermore the traction drive unit is used under high-speed and high-load conditions. Hence a traction drive fluid for use in the traction drive mechanism is desired to be of low viscosity and to be capable of maintaining a high traction coefficient even at elevated temperatures, that is, to be able to use satisfactorily under such severe conditions.

Various compounds have heretofore been proposed as traction drive fluids, including the compounds as described in Japanese Patent Publication Nos. 338/1971, 339/1971, 35763/1972, 42067/1973, 42068/1973, and 36105/1978, and Japanese Patent Application Laid-Open Nos. 43108/1980 and 40726/1980. These compounds, however, have disadvantages in that the traction coefficient drops as the temperature rises, or although the traction coefficient does not drop, the viscosity is high and the stirring loss in the traction drive mechanism is large.

SUMMARY OF THE INVENTION

An object of the invention is to provide a fluid for traction drive which is free from the problems as described above and meets various requirements.

The present invention relates to a fluid for traction drive which contains as a base stock a liquid material prepared by bringing naphthalene or tetralin into contact with a Friedel-Crafts catalyst and, thereafter, hydrogenating resultant compounds.

BRIEF DESCRIPTION OF THE DRAWINGS

FIG. 1 is a graph showing the temperature dependence of traction coefficient for the products obtained in Examples and a Comparative Example.

DETAILED DESCRIPTION OF THE INVENTION

When naphthalene or tetralin is brought into contact with a Friedel-Crafts catalyst and then is hydrogenated, various compounds are produced. Main compounds obtained herein are the hydrogenated products of a dimer of naphthalene or tetralin, or the hydrogenated products of a ring-opened dimer of naphthalene or tetralin. Typical examples of the former hydrogenated products include 1,1'-bisdecalin represented by the formula (I) and 1,2'-bisdecalin represented by the formula (II).

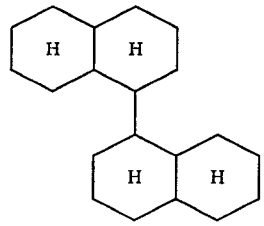

Formula (I)

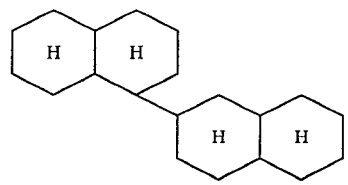

Formula (II)

An example of the latter hydrogenated products includes 1-decalyl-4-cyclohexylbutane.

Conditions under which the starting material, naphthalene or tetralin, is brought into contact with the Friedel-Crafts catalyst are not critical in the present invention; various conditions can be employed. Usually the starting material is brought into contact with the Friedel-Crafts catalyst at a temperature of from $-30°$ to $+80°$ C. under atmospheric pressure.

Friedel-Crafts catalysts which can be used include $AlCl_3$, $FeCl_3$, $SnCl_4$, $ZnCl_2$, $HF$ and $H_2SO_4$. Of these compounds, aluminum chloride ($AlCl_3$) is particularly preferred.

At this contact reaction step, alkenyl halide such as methallyl chloride and allyl chloride, and alkyl dihalide such as 1,2-dichloropropane and 2,3-dichlorobutane can be added to the reaction system. Dienes such as isoprene and butadiene can be added in place of the alkenyl halide or alkyl dihalide.

When the starting material, naphthalene or tetralin, is reacted with the alkenyl halide or alkyl dihalide as described above in the presence of the Friedel-Crafts catalyst and, thereafter, resultant compounds are hydrogenated, there are obtained compounds represented by the general formula (III) along with the hydrogenated products of a dimer of naphthalene or tetralin, such as the compounds represented by the formulae (I) and (II), and the hydrogenated products of a ring-opened dimer of naphthalene or tetralin.

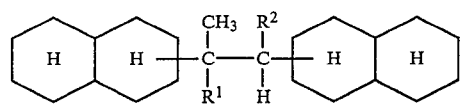

(wherein $R^1$ and $R^2$ are each a hydrogen atom or a methyl group).

Typical examples of the compounds represented by the formula (III) are as follows:

1,2-Di(1-decalyl)propane represented by the formula (IV):

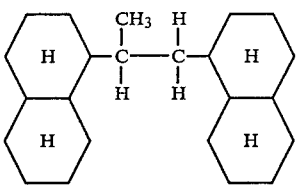

1-(2-Decalyl)-2-(1-decalyl)propane represented by the formula (V):

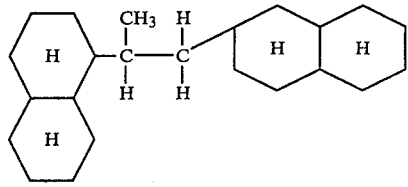

1-(1-Decalyl)-2-(2-decalyl)propane represented by the formula (VI):

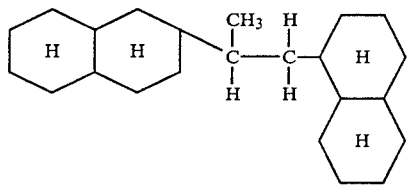

1,2-Di(2-decalyl)propane represented by the formula (VII):

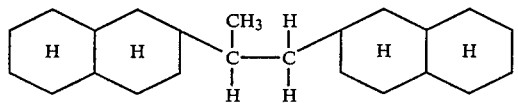

2,3-Di(1-decalyl)butane represented by the formula (VIII):

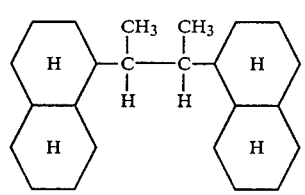

2-(1-Decalyl)-3-(2-decalyl)butane represented by the formula (IX):

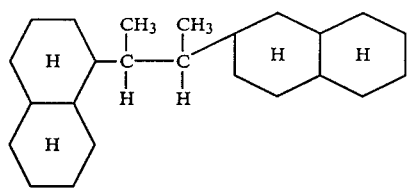

2,3-Di(2-decalyl)butane represented by the formula (X):

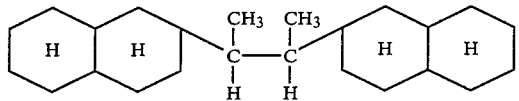

2-Methyl-1,2-di(1-decalyl)propane represented by the formula (XI):

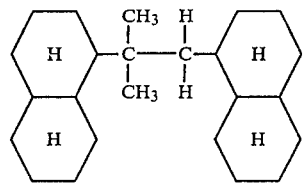

2-Methyl-1-(2-decalyl)-2-(1-decalyl)propane represented by the formula (XII):

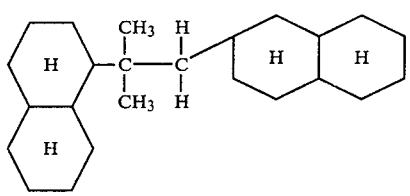

2-Methyl-1-(1-decalyl)-2-(2-decalyl)propane represented by the formula (XIII):

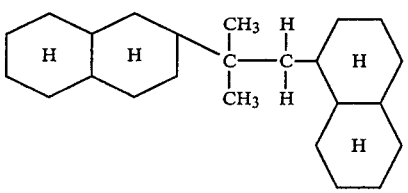

2-Methyl-1,2-di(2-decalyl)propane represented by the formula (XIV):

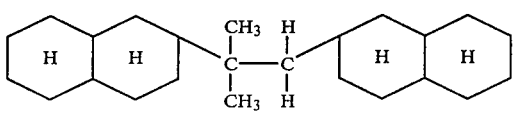

2-Methyl-2,3-di(1-decalyl)butane represented by the formula (XV):

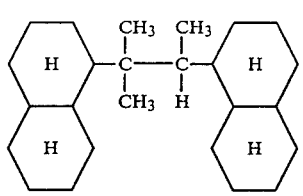

2-Methyl-2-(2-decalyl)-3-(1-decalyl)butane represented by the formula (XVI):

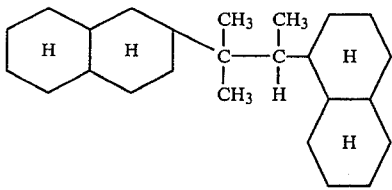

2-Methyl-2-(1-decalyl)-3-(2-decalyl)butane represented by the formula (XVII):

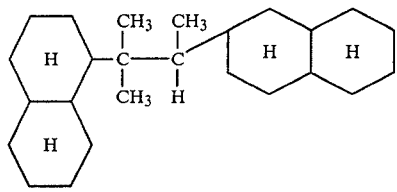

2-Methyl-2,3-di(2-decalyl)butane represented by the formula (XVIII):

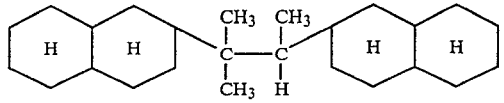

In reacting the starting material, naphthalene or tetralin, with the alkenyl halide or alkyl dihalide in the presence of the Friedel-Crafts catalyst, the ratio of the naphthalene or tetralin to the alkenyl halide or alkyl dihalide cannot be determined unconditionally because it varies depending on the desired product and the reaction conditions employed. Usually the amount of the alkenyl halide or alkyl dihalide used is from 0.05 to 1 moles per mole of the naphthalene or tetralin, with the range of from 0.1 to 0.3 moles being preferred.

Hydrogenation of the reaction products as obtained above produces, the compounds represented by the formula (III) along with the hydrogenated products of a dimer of naphthalene or tetralin or the hydrogenated products of a ring-opened dimer of naphthalene or tetralin. The ratio of the compounds represented by the formula (III) to the hydrogenated products of a dimer of naphthalene or of a ring-opened dimer of naphthalene or tetralin varies depending on the reaction conditions employed. For example, when aluminum chloride (AlCl$_3$) is used as the Friedel-Crafts catalyst, the proportion of the hydrogenated products of a dimer of naphthalene or tetralin or of a ring-opened dimer of naphthalene or tetralin increases, and when ferric chloride (FeCl$_3$) is used as the Friedel-Crafts catalyst, the proportion of the compounds represented by the formula (III) increases.

The hydrogenation process is generally performed at a temperature of from 50° to 250° C. under a pressure of from 10 to 150 kg/cm$^2$ in the presence of a hydrogenation catalyst. It is also effective that the reaction product (i.e. the compounds produced by bringing naphthalene or tetralin into contact with a Friedel-Crafts catalyst) is previously distilled to collect a fraction having a boiling point of from 165° to 175° C./0.1 mmHg and, thereafter, the fraction is hydrogenated. As hydrogenation catalysts, common hydrogenation catalysts containing platinum, palladium, nickel, rhodium, ruthenium, etc. as an active ingredient can be used. In particular, the hydrogenation using a catalyst containing platinum or ruthenium produces a product showing superior performance.

The liquid material as obtained by the hydrogenation process contains large amounts of the hydrogenated products of a dimer of naphthalene or tetralin or the hydrogenated products of a ring-opened dimer of naphthalene or tetralin. When the alkenyl halide or alkyl dihalide is used, the liquid material contains large amounts of the compounds represented by the formula (III) and further other various compounds.

In the present invention, naphthalene or tetralin derivatives, i.e., naphthalene or tetralin containing at least one alkyl group such as a methyl group, an ethyl group, and a propyl group, can be used as the starting material. In this case, the corresponding products, i.e., the hydrogenated products of a dimer of naphthalene or tetralin derivative or the hydrogenated products of a ring-opened dimer of naphthalene or tetralin derivative, and the derivatives of the compounds represented by the formula (III), are obtained.

The thus-prepared liquid material can be used in itself as a base stock for the traction drive fluid of the present invention. The traction drive fluid of the invention shows a superior traction coefficient, i.e., the traction coefficient varies only slightly over a temperature range from low temperature to elevated temperature (from room temperature to 140° C.), and further the traction drive fluid of the invention has a low viscosity.

In particular, when naphthalene or tetralin is brought into contact with the Friedel-Crafts catalyst, and the resultant compounds are distilled to collect a fraction having a boiling range of from 165° to 175° C./0.1 mmHg, and then the fraction is hydrogenated, the obtained liquid material is excellent as the base stock for the traction drive fluid of the invention.

The traction drive fluid of the invention is of low cost because the liquid material can be prepared inexpensively.

The traction drive fluid of the invention exhibits a superior traction coefficient from low temperature to elevated temperature. Hence it contributes to the production of small-sized drive mechanisms, and further can be used under severe conditions of high-speed and high-load. Thus the traction drive fluid of the invention can be used widely in various machines such as cars, continuously variable transmission, and hydraulic machines.

The present invention is described in greater detail with reference to the following Examples and Comparative Examples.

EXAMPLE 1

A mixture of 3,960 grams of tetralin and 100 grams of anhydrous aluminum chloride was placed in a 5-liter glass flask and stirred at room temperature for 3 hours. At the end of the time, 700 milliliters of water was introduced into the flask to decompose the aluminum chloride. The thus-formed oil layer was separated, washed three times with 1 liter of a 2 normal aqueous solution of sodium hydroxide and 1 liter of a saturated brine (NaCl) and, thereafter, dried over anhydrous sodium sulfate. The resulting oil material was distilled to remove the unreacted tetralin and, thereafter, vacuum-distilled to obtain 700 grams of a fraction, b.p., 165°–175° C./0.1 mmHg.

Then 500 milliliters of the fraction as obtained above was placed in a 1-liter autoclave and 50 grams of an activated nickel catalyst for hydrogenation (trade name: N=112 Catalyst, produced by Nikki Kagaku Co., Ltd.) was added. The fraction was hydrogenated at a temperature of 200° C. under a hydrogen pressure of 50 kilograms per square centimeter. The reaction mixture was cooled and filtered to separate the catalyst.

A light fraction was removed from the reaction product by stripping and the product was analyzed. This analysis showed that the degree of hydrogenation was 99.9% or more, and that the product was composed mainly of a mixture of the hydrogenated products of a dimer of tetralin, such as 1,2'-bisdecalin and 1,1'-bisdecalin, and the hydrogenated products of a ring-opened dimer of tetralin, such as 1-decalyl-4-cyclohexylbutane. The specific gravity of the product was 0.95 (15/4° C.); the dynamic viscosity was 72 centistokes (40° C.) and 6.5 centistokes (100° C.); and the viscosity index was −20.

The traction coefficient of the product was measured over a temperature range from 40° to 120° C. The results are shown in FIG. 1.

The traction coefficient was measured by the use of two-roller machine. One of the same size (diameter: 60 millimeters; thickness: 6 millimeters) of two rollers in contact on one line was rotated at a fixed rate (2,000 revolutions per minute), and the other roller was rotated at a predetermined lower rate (1,700 revolutions per minute). A load of 140 kilograms was applied on the contact portion of the two rollers by means of a spring, and the torque was measured with a strain gage and a torque meter to determine the traction coefficient. The rollers were made of carbon steel SCM-3, and the surface of which was subjected to a buffing treatment with alumina (0.03 micron). The surface roughness was Rmax=0.2 micron and the Hertzian pressure in contact was 75 kilograms per square millimeter. In measuring the traction coefficient, the oil temperature was changed from room temperature to elevated temperatures by heating an oil tank with a heater.

EXAMPLE 2

A mixture of 3,960 grams of tetralin and 100 grams of anhydrous aluminum chloride was placed in a 5-liter glass flask, and the temperature in the flask was lowered to 10° C. with ice water. Then 453 grams of methallyl chloride was slowly dropped thereto over 5 hours while stirring, and the resulting mixture was stirred for 1 hour to complete the reaction. At the end of the time, 700 milliliters of water was introduced into the flask to decompose the aluminum chloride. The thus-formed oil layer was separated, washed three times with 1 liter of a 2 normal aqueous solution of sodium hydroxide and 1 liter of a saturated brine (NaCl), and then dried over anhydrous sodium sulfate. The resulting oil material was distilled to remove the unreacted tetralin and, thereafter, vacuum-distilled to obtain 700 grams of a fraction, b.p., 165°–175° C./0.1 mmHg.

The fraction as obtained above was analyzed. This analysis confirmed that the fraction was composed mainly of a mixture of the hydrogenated products of a dimer of the starting material, such as 1,2'-bistetralin and 1,1'-bistetralin, the hydrogenated products of a ring-opened dimer of tetralin, such as 1-tetralyl-4-phenylbutane, and 2-methyl-1,2-ditetralylpropanes.

Then 500 milliliters of the fraction was placed in a 1-liter autoclave and 50 grams of an activated nickel catalyst for hydrogenation (trade name: N=112 Catalyst, produced by Nikki Catalyst Co., Ltd.) was added thereto. The fraction was hydrogenated at a temperature of 200° C. under a hydrogen pressure of 50 kilograms per square centimeter. The reaction mixture was cooled and filtered to remove the catalyst.

A light fraction was removed from the reaction product by stripping and the product was analyzed. This analysis confirmed that the degree of hydrogenation was 99.9% or more, and that the product was composed mainly of a mixture of (a) the hydrogenated products of a dimer of the starting material, such as 1,2'-bisdecalin and 1,1'-bisdecalin, (b) the hydrogenated products of a ring-opened dimer of tetralin, such as 1-decalyl-4-cyclohexylbutane, and (c) 2-methyl-1,2-didecalylpropanes (the molar ratio of (a), (b) and (c) being 2:4:1). The specific gravity of the product was 0.95 (15/4° C.); the dynamic viscosity was 65 centistokes (40° C.) and 6.2 centistokes (100° C.); and the viscosity index was −11.

The traction coefficient of the product was measured over a temperature range from 30° to 120° C. in the same manner as in Example 1. The results are shown in FIG. 1.

COMPARATIVE EXAMPLE 1

A mixture of 1,000 grams of α-methylstyrene, 50 grams of acidic terra abla, and 50 grams of ethylene glycol was placed in a 3-liter glass flask and reacted at 140° C. for 2 hours while stirring. The reaction mixture was filtered to remove the catalyst and distilled to separate the unreacted α-methylstyrene and ethylene glycol whereby 900 grams of a fraction, b.p., 125°–130° C./0.2 mmHg, was obtained.

NMR analysis and gas chromatographic analysis confirmed that the fraction as obtained above was a mixture of 95% of a linear dimer of α-methylstyrene and 5% of a cyclic dimer of α-methylstyrene.

The fraction was hydrogenated in the same manner as in Example 2 and also was subjected to the same post-treatment as in Example 2, whereby a traction drive fluid composed mainly of 2,4-dicyclohexyl-2-methylpentane was obtained.

The specific gravity of the traction drive fluid was 0.90 (15/4° C.); the dynamic viscosity was 22 centistokes (40° C.) and 3.7 centistokes (100° C.); and the viscosity index was 16.

The traction coefficient of the traction drive fluid was measured over a temperature range from 25° to 120° C. in the same manner as in Example 1. The results are shown in FIG. 1.

COMPARATIVE EXAMPLE 2

2,2'-Binaphthyl (50 grams) was placed in a 200-milliliter autoclave and 5 grams of an activated nickel catalyst for hydrogenation (trade name: N-112 Catalyst, produced by Nikki Kagaku Co., Ltd.) was added thereto. Then the 2,2'-binaphthyl was hydrogenated at a temperature of 200° C. under a hydrogen pressure of 50 kilograms per square centimeter. The reaction mixture was cooled and filtered to separate the catalyst.

A light fraction was removed from the reaction product by stripping and the product was analyzed. This analysis confirmed that the degree of hydrogenation was 99.9% or more and the product was 2,2'-bisdecalin. The specific gravity of the product was 0.95 (15/4° C.); the dynamic viscosity was 250 centistokes (40° C.) and 11 centistokes (100° C.); and the viscosity index was −97.

As apparent from the foregoing results, the 2,2′-bisdecalin has a viscosity much higher than that (20–100 centistokes (40° C.)) generally required for lubricating oils and, therefore, is not suitable for use as a lubricating oil. That is, it can be seen that the 2,2′-bisdecalin is inferior to the hydrogenated products as obtained in Examples 1 and 2.

EXAMPLE 3

A mixture of 3,960 grams of tetralin and 120 grams of anhydrous ferric chloride was placed in a 5-liter flask, and 634 grams of methallyl chloride was gradually dropped over 8 hours while stirring at room temperature. They were reacted by further stirring for 1 hour. Then 1 liter of water was added thereto, and the thus-formed oil layer was separated, washed three times with 1 liter of a 1 normal aqueous solution of NaOH and 1 liter of a saturated brine (NaCl), and dried over anhydrous sodium sulfate. The resulting oil material was distilled to remove the unreacted tetralin and, thereafter, vacuum-distilled to obtain 500 grams of a fraction, b.p., 165°–195° C./0.12 mmHg. This fraction was composed mainly of 2-methyl-1,2-ditetralylpropanes.

The fraction was placed in a 1-liter autoclave and 50 grams of an activated 0.5% platinum-alumina catalyst (produced by Japan Engelhard Co., Ltd.) was added thereto. Then the fraction was hydrogenated at a temperature of 200° C. under a hydrogen pressure of 50 kilograms per square centimeter (by gauge) for 4 hours. A light fraction was removed from the reaction product as obtained above and the product was analyzed. This analysis confirmed that the product was composed mainly of a mixture of (a) 2-methyl-1,2-didecalylpropanes, (b) bisdecalin such as 1,1′-bisdecalin and 1,2′-bisdecalin, and (c) 1-decalyl-4-cyclohexylbutanes (the molar ratio of (a), (b) and (c) being 8:1:1).

The refractive index of the product was $n_D^{20} = 1.5123$; the specific gravity was 0.96 (15/4° C.); and the dynamic viscosity was 13 centistokes (100° C.).

The traction coefficient was measured over a temperature range from 50° to 140° C. in the same manner as in Example 1. The results are shown in FIG. 1.

EXAMPLE 4

The procedure of Example 3 was repeated with the exception that 100 grams of aluminum chloride was used in place of the anhydrous ferric chloride, 383 grams of allyl chloride was used in place of the methallyl chloride, and the reaction temperature was changed to 10° C., whereby 750 grams of a fraction having a boiling point of from 155° to 175° C./0.1 mmHg.

Then 500 grams of the fraction was hydrogenated in the same manner as in Example 3 to obtain 550 grams of a product composed mainly of a mixture of (a) 1,2-didecalylpropanes, (b) 1-decalyl-4-phenylbutane and (c) 1,2′-bisdecalin (the molar ratio of (a), (b) and (c) being 4:4:1). The refractive index of the product was $n_D^{20} = 1.5066$; the specific gravity was 0.94 (15/4° C.); and the dynamic viscosity was 7.5 centistokes (100° C.).

The traction coefficient was measured over a temperature range from 30° to 130° C. in the same manner as in Example 1. The results are shown in FIG. 1.

What is claimed is:

1. A process for improving the coefficient of traction between at least two relatively rotatable elements in a torque transmitting relationship and for maintaining said coefficient of traction substantially constant over a broad range of operating temperatures which comprises introducing between the tractive surfaces of said elements a traction drive fluid comprising as the active component at least one compound selected by the general formulae (I), (II) and (III):

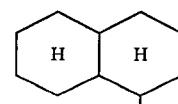
(I)

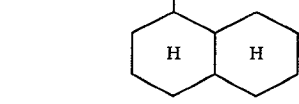
(II)

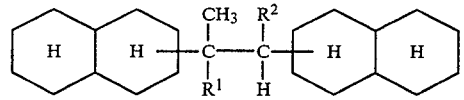
(III)

wherein $R_1$ and $R_2$ are each a hydrogen or methyl group, said traction drive fluid being essentially free of 2,2′-bisdecalin.

2. A process according to claim 1 in which the active component comprises a mixture of compounds (I) and (II).

3. A process according to claim 1 in which the active component is a mixture of compounds (I), (II) and (III).

4. A process according to claim 3 in which the combined proportion of compounds (I) and (II) is greater than that of compound (III).

5. A process according to claim 3 in which the proportion of compound (III) is greater than the combined proportion compound (I) and (II).

6. A traction drive fluid composition for use between two relatively rotatable elements in a torque transmitting relationship which comprises as the active component at least one compound represented by the formulae (I), (II) and (III):

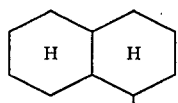
(I)

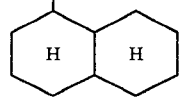
(II)

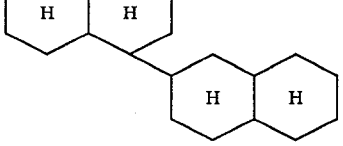

-continued

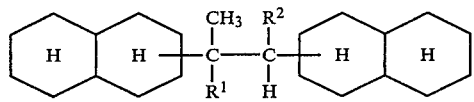 (III)

wherein $R_1$ and $R_2$ are each a hydrogen or methyl group, said traction drive fluid being essentially free of 2,2'-bisdecalin.

7. A traction drive fluid composition according to claim 6 in which the active component comprises a mixture of compounds (I) and (II).

8. A traction drive fluid composition according to claim 6 in which the active component comprises a mixture of compounds (I), (II) and (III).

9. A traction drive fluid composition according to claim 8 in which the combined proportion of compounds (I) and (II) is greater than that of compound (III).

10. A traction drive fluid composition according to claim 8 in which the proportion of compound (III) is greater than the combined proportion of compounds (I) and (II).

* * * * *